United States Patent [19]
Frezza

[11] Patent Number: 5,848,881
[45] Date of Patent: Dec. 15, 1998

[54] LIQUID DRUG INFUSION PUMP

[75] Inventor: Pierre Frezza, Charly, France

[73] Assignee: Compagnie de Developpement Aguettant Parc Scientifique Tony-Garnier, Lyons, France

[21] Appl. No.: 875,479
[22] PCT Filed: Nov. 29, 1996
[86] PCT No.: PCT/FR96/01906
§ 371 Date: Sep. 24, 1997
§ 102(e) Date: Sep. 24, 1997
[87] PCT Pub. No.: WO97/19716
PCT Pub. Date: Jun. 5, 1997

[30] Foreign Application Priority Data

Nov. 30, 1995 [FR] France .................................. 95 14456

[51] Int. Cl.$^6$ .................................................. F04B 39/10
[52] U.S. Cl. ........................ 417/560; 417/566; 137/102; 137/512.4
[58] Field of Search ..................... 417/560, 566, 417/570, 571; 137/102, 218, 512.4

[56] References Cited

U.S. PATENT DOCUMENTS 4,737,083  4/1988  Meyer ...................................... 417/566
5,503,538  4/1996  Wiernicki et al. ...................... 417/560

FOREIGN PATENT DOCUMENTS

A 2-689014  10/1993  France .

*Primary Examiner*—Timothy Thorpe
*Assistant Examiner*—Cheryl J. Tyler
*Attorney, Agent, or Firm*—Oliff & Berridge, PLC

[57] ABSTRACT

A pump including a first portion (2) with a metering cylinder (3) containing a plunger (4), and a second portion (7) engaging the surface of the first portion (2) in which the outlet of the cylinder (3) is located, and comprising a recess (10) located opposite the cylinder for delivering a liquid. A flexible impervious membrane (8) clamped between the two portions (2, 7) comprises an opening (13) facing the cylinder (3) and a resilient circumferential ring (12) engaging the bottom of the recess (10). A disc (14) in the central area of the recess engages the membrane (8), and a duct (6) linked to the cylinder (5) and having an outlet in the same surface of the first portion (2) as the cylinder (5) is connected to a liquid discharge tubing.

4 Claims, 2 Drawing Sheets

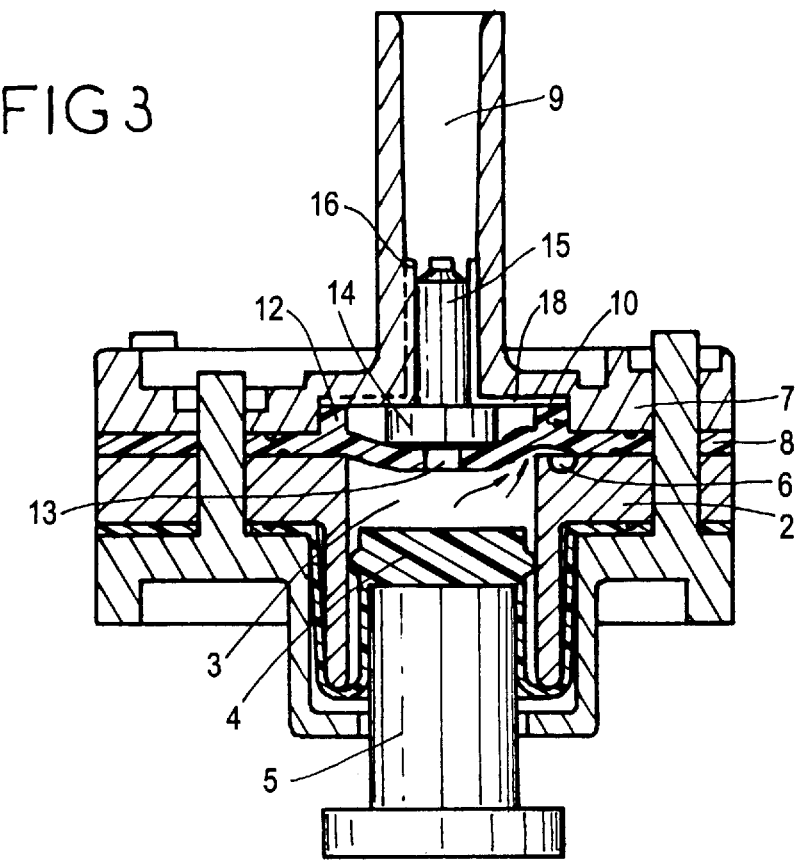
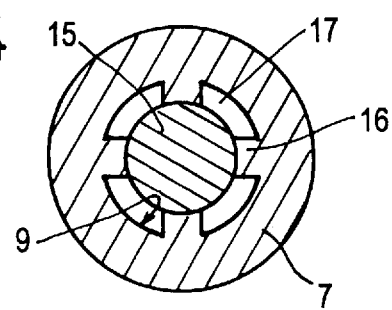

LIQUID DRUG INFUSION PUMP

BACKGROUND OF THE INVENTION

The present invention relates to a infusion pump for medical liquids.

The document FR-A-2 689 014, in the name of the Applicant company, describes a infusion pump for medical liquids which comprises at least one device with cylinder and plunger for suctioning a liquid from a container and driving the liquid back into a tubing connected to the patient.

This infusion pump comprises:

a first component in which there is formed at least one metering cylinder which, containing a plunger driven in a reciprocating movement, opens out in one of the faces of the component, perpendicular to this face, a second component which, bearing on that face of the first component in which each cylinder opens out, includes, in line with each cylinder, a recess of a diameter greater than that of the corresponding cylinder, and communicating with a container for supply of liquid, an impermeable and elastically deformable membrane held securely between the two components and including an orifice in line with each cylinder, a disk lodged in each recess of the second component, of which that face directed toward the first component is stepped and comprises an external part which bears, via the membrane, on that face of the first component in which the corresponding cylinder opens out, just around this cylinder, and a central part projecting in the direction of the inside of the cylinder, this disk including through-holes which are uniformly distributed and are arranged in proximity to its periphery, a spring exerting a pressure on the disk in the direction of the first component, and associated with each cylinder, a duct opening out in the same face of the first component as the cylinder in question, this duck, associated with a removal tubing formed in this component, being arranged in proximity to the metering cylinder, in line with the recess of the second component, but beyond the disk which this recess contains, and being covered by the membrane held securely between the two components.

In the known pump it is necessary to provide a spring exerting a pressure on the disk in the direction of the first component. The presence of this spring has the disadvantage that a metal material comes into contact with the medical liquid transferred via the pump. In addition, the presence of this spring above the disk necessitates that the disk be guided in the area of the periphery thereof in the recess formed in the first component, which leads to a stepped disk structure, and to the provision of through-holes in the disk, in proximity to its periphery, in order to permit the passage of the medical liquid.

OBJECTS AND SUMMARY OF THE INVENTION

A first object of the invention is to make available a infusion pump for medical liquids, in which the spring which bears on the disk in order to guarantee that the latter is impermeable can be omitted.

Another object of the invention is to simplify the structure of the disk bearing against the membrane.

To this end, the infusion pump for medical liquids to which the invention relates, of the type comprising:

a first component in which there is formed a metering cylinder which, containing a plunger driven in a reciprocating movement, opens out in one of the faces of the component, perpendicular to this face, a second component which, bearing on that face of the first component in which the cylinder opens out, includes, in line with the latter, a recess of a diameter greater than that of the cylinder, and communicating with a container for supply of liquid, an impermeable and elastically deformable membrane held securely between the two components and including an orifice in line with the cylinder, a disk lodged in the recess of the second component, of which that face directed toward the first component bears on the membrane, associated with the cylinder, a duct opening out in the same face of the first component as the cylinder, this duct, associated with a removal tubing formed in this component, being arranged in proximity to the cylinder, in line with the same recess of the second component, but beyond the metering cylinder, and being covered by the membrane held securely between the two components, is characterized in that the membrane includes, on its face situated toward the supply of the liquid and in the zone of the recess formed in the second component outside the metering cylinder, an elastic ring molded with the membrane and bearing on the bottom of the recess formed in the second component, the disk bearing on the membrane being of a diameter smaller than that of this recess and including central guiding means.

The presence of the ring on the membrane forming a flap valve replaces the known metal spring in the device in the document cited in the introduction. The compression of this elastic ring creates the impermeability of the chamber at the discharge pressure used.

This structure has the advantage of omitting a component, namely the spring, and of having no metal material in contact with the liquid. In addition, the size of the disk can be reduced, and the disk can be guided via its center, given that there is no longer any spring acting in the area of this center.

According to one embodiment of this pump, the central guiding means of the disk consist of a rod which is perpendicular to the disk and which is guided in translation in the conduit for supply of the liquid.

In this case, the guide rod of the disk is advantageously of a smaller diameter than the diameter of the conduit for supply of the liquid, and this conduit includes, at least in its zone opening out into the pump, axial ribs projecting from its inner wall and delimiting, on the one hand, a central zone for guiding the rod of the disk and, on the other hand, channels for the passage of the liquid.

According to another characteristic of the invention, the channels formed in the wall of the conduit for supply of the liquid are continued via radial channels formed in the bottom of the recess of the second component and opening out beyond the periphery of the disk.

In any event, the invention will be clearly understood with the aid of the following description, in which reference is made to the attached diagrammatic drawing which represents, by way of a nonlimiting example, one embodiment of this pump:

DESCRIPTION OF THE DRAWINGS

FIGS. 1 to 3 are three longitudinal sections through the pump during three operating phases;

FIG. 4 is a transverse section through the pump, and on an enlarged scale, along the line IV—IV in FIG. 1.

DETAILED DESCRIPTION OF THE INVENTION

Figure 1:
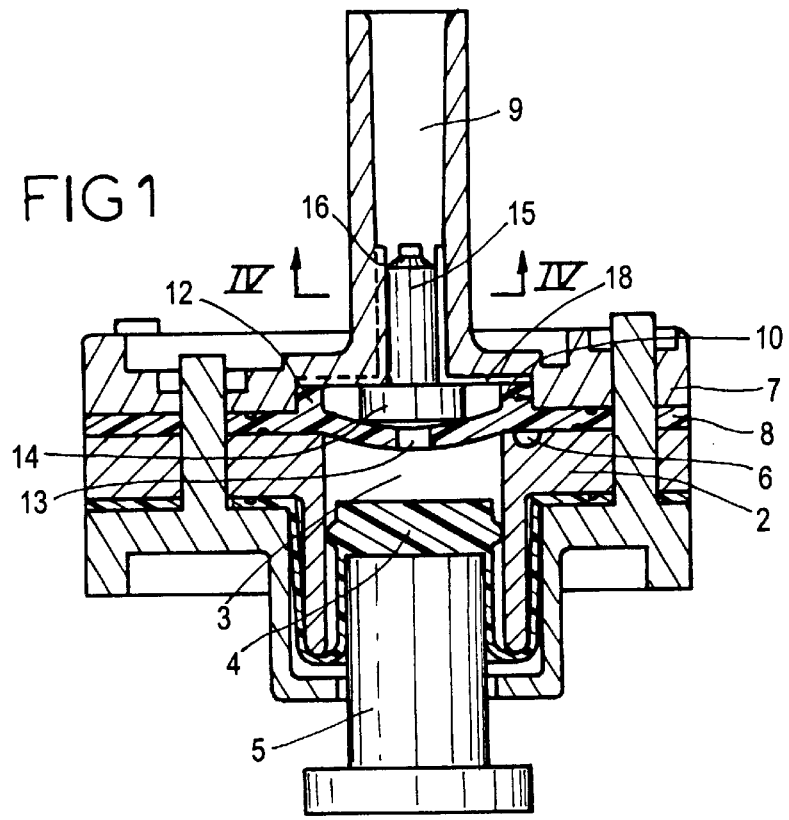

The infusion pump represented in the drawing comprises a first component 2 inside which a metering cylinder 3 is formed. Inside this metering cylinder, a plunger 4 is mounted so as to be axially displaceable under the action of a drive mechanism which is shown diagrammatically and is designated by the reference 5. A duct 6 opens out in the upper face of the component 2, in proximity to the metering cylinder 3, this duct 6 being associated with a removal tubing (not shown) for the infusion liquid. The first component 2 is covered by a second component 7, mounted with interposition of an impermeable membrane 8. The second component 7 is continued at its center by a conduit 9 for supply of the infusion liquid. Formed in the central part of the second component 7 there is a recess 10 which is of a diameter greater than the diameter of the metering cylinder 3 and of which the peripheral wall is situated beyond the duct 6 for removal of the liquid. The membrane 8, which is held securely between the components 2 and 7, includes, on its face situated toward the supply of the liquid, and in the zone of the recess 10 situated outside the metering cylinder 3, a molded elastic ring 12 bearing on the bottom of the recess 10.

The membrane 8 also has a central orifice 13. Mounted inside the recess 10 there is a disk 14 which bears against that face of the membrane directed toward the supply of the liquid. As is shown in the drawing, this disk 14 is of a diameter smaller than that of the recess 10. This disk 14 comprises, projecting from its center, a rod 15 which is engaged in the conduit 9. To be able to guide the rod 15 in the conduit 9, the latter includes axial ribs 16 in its zone adjacent to the pump, the rod being guided in the central part between the ribs 16, and these ribs delimiting between each other channels 17 permitting the passage of liquid. These channels 17 are continued via radial channels 18 formed in the bottom of the recess 10 of the second component 7, these channels opening out beyond the periphery of the disk 14.

Figure 2:
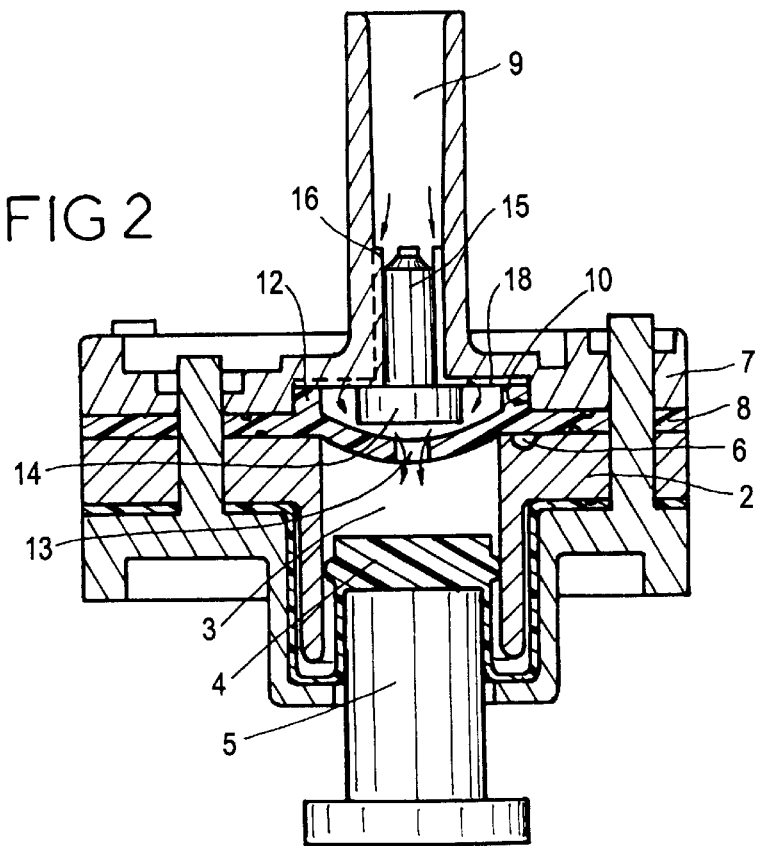

The pump according to the invention operates in the following way. When the pump is in a static state, the membrane 8 is pressed flat against the disk 14 and the orifice 13 is closed by the disk. When the plunger 4 is displaced downward, as is shown in FIG. 2, a partial vacuum is produced and detaches the central part of the membrane 8 from the disk 14, with liquid flowing from the conduit 9 into the channels 17, 18, then through the orifice 13 into the metering cylinder 3. At this point, the membrane is pressed flat against the first component 2 and does not permit communication between the metering cylinder 3 and the duct 6 for removal of the liquid.

In the next phase of the cycle, when the plunger rises, the liquid pressure inside the metering chamber presses the membrane flat against the disk and ensures an upward deformation of the membrane in order to permit the passage of liquid from the metering chamber toward the duct 6 for discharge of the liquid.

As will be evident from the above, the invention brings a great improvement to the existing technique by making available a infusion pump in which the design of the membrane guarantees the elastic recovery of the latter during the pressure differences to which it is subjected by the liquid.

It goes without saying that the invention is not limited to the single embodiment of this pump described hereinabove by way of example, and instead embraces all variations thereof. Thus, in particular, the guide means of the disk could be different, without thereby departing from the scope of the invention.

I claim:

1. An infusion pump for medical liquids comprising:
   a first component having a plurality of faces, said first component having a metering cylinder formed therein, said metering cylinder containing a plunger driven in a reciprocating manner and having an opening perpendicular to one of the faces of said first component;
   a duct disposed on said perpendicular face of said first component;
   a second component disposed on said perpendicular face of said first component, communicating with a container to supply a liquid thereto, and having a recess, said recess being coaxial with said second component and having a diameter greater than that of said metering cylinder;
   an impermeable and elastically deformable membrane securely held between said first and second components, said membrane including an elastic ring molded thereto and an aperture coaxial with said metering cylinder;
   said elastic ring of said membrane forced against the bottom of said recess; and
   a disk disposed in said recess of said second component having a diameter smaller than the recess diameter and further including central guiding means, said disk disposed proximal said metering cylinder, coaxial with said recess of said second component, and covered by said membrane.

2. The infusion pump according to claim 1, wherein said central guiding means comprises a guide rod perpendicular to said disk and said rod is guided in translation in a conduit to supply liquid to the pump.

3. The infusion pump according to claim 2, wherein said guide rod has a smaller diameter than the diameter of said conduit, and said conduit further including axial ribs projecting from an inner wall of the conduit and delimiting a central zone for guiding said guide rod and channels for the passage of the supply liquid.

4. The infusion pump according to claim 3, wherein said channels formed in said inner wall of said conduit extend to form radial channels in the bottom of said recess and said radial channels open beyond the periphery of said disk.

\* \* \* \* \*